United States Patent [19]

Berg

[11] Patent Number: 5,779,862
[45] Date of Patent: *Jul. 14, 1998

[54] SEPARATION OF 2-METHYL-1-BUTANOL AND 3-METHYL-1-BUTANOL FROM 1-PENTANOL BY AZEOTROPIC DISTILLATION

[76] Inventor: Lloyd Berg, 1314 S. 3rd Ave., Bozeman, Mont. 59715

[*] Notice: The term of this patent shall not extend beyond the expiration date of Pat. No. 5,407,541.

[21] Appl. No.: 819,645

[22] Filed: Mar. 17, 1997

[51] Int. Cl.⁶ .................. B01D 3/36; C07C 29/82
[52] U.S. Cl. .................. 203/57; 203/58; 203/59; 203/60; 203/62; 203/63; 203/65; 203/67; 203/69; 203/70; 568/913
[58] Field of Search .................. 203/57, 62, 58, 203/60, 63, 68, 65, 59, 67, 69, 70; 568/913

[56] References Cited

U.S. PATENT DOCUMENTS

| | | | |
|---|---|---|---|
| 4,969,977 | 11/1990 | Berg | 203/60 |
| 5,160,414 | 11/1992 | Lee et al | 568/913 |
| 5,407,541 | 4/1995 | Berg | 203/63 |
| 5,417,813 | 5/1995 | Berg | 203/60 |
| 5,437,770 | 8/1995 | Berg | 203/58 |
| 5,439,561 | 8/1995 | Berg | 203/63 |
| 5,447,608 | 9/1995 | Berg | 203/57 |
| 5,645,695 | 7/1997 | Berg | 203/60 |
| 5,658,435 | 8/1997 | Berg | 203/62 |

FOREIGN PATENT DOCUMENTS 0047204  3/1982  European Pat. Off. ........ 203/57

*Primary Examiner*—Virginia Manoharan

[57] ABSTRACT

2-Methyl-1-butanol and 3-methyl-1-butanol are difficult to separate from 1-pentanol by conventional distillation or rectification because of the proximity of their boiling points. 2-Methyl-1-butanol and 3-methyl-1-butanol can be easily separated from 1-pentanol by azeotropic distillation. Effective agents are toluene, methyl acetate and tetrahydrofuran.

1 Claim, No Drawings

SEPARATION OF 2-METHYL-1-BUTANOL AND 3-METHYL-1-BUTANOL FROM 1-PENTANOL BY AZEOTROPIC DISTILLATION

FIELD OF THE INVENTION

This invention relates to a method for separating 2-methyl-1-butanol and 3-methyl-1-butanol from 1-pentanol using certain organic liquids as the agent in azeotropic distillation.

DESCRIPTION OF PRIOR ART

Azeotropic distillation is the method of separating close boiling compounds or azeotrones from each other by carrying out the distillation in a multiplate rectification column in the presence of an added liquid, said liquid forming an azeotrope with one or more of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theorietical Stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

2-Methyl-1-butanol and 3-methyl-1-butanol both boil at 130 C. and cannot be separated from each other by distillation. 1-Pentanol boils at 136 C., only six degrees apart and the relative volatility between 1-pentanol and the two methyl butanols is 1.14, making it impossible to separate 1-pentanol from the methyl butanols by conventional rectification. Table 2 shows that with an agent giving a relative volatility of 1.55, only 28 actial plates are required to get 99% purity.

TABLE 2

Theoretical and Actual Plates Required vs. Relative Volatility for 2-Methyl-1-butanol and 3-Methyl-1-butanol from 1-Pentanol Separation

| Relative Volatility | Theoretical Plates Required At Total Reflux, 99% Purity | Actual Plates Required, 75% Eff. |
|---|---|---|
| 1.28 | 38 | 51 |
| 1.45 | 25 | 34 |
| 1.55 | 21 | 28 |

OBJECTIVE OF THE INVENTION

The object of this invention is to provide a process or method of azeotropic distillation that will enhance the relative volatility of 2-methyl-1-butanol and 3-methyl-1-butanol from 1-pentanol in their separation in a rectification column. It is a further object of this invention to identify effective azeotropic distillation agents that are stable and can be recycled.

SUMMARY OF THE INVENTION

The objects of the this invention are provided by a process for the separation 2-methyl-1-butanol and 3methyl-1-butanol from 1-pentanol which entails the use of ceratin organic compounds when employed as the agent in azeotropic distillation.

TABLE 3

Effective Azeotropic Distillation Agents For Separating 2-Methyl-1-butanol & 3-Methyl-1-butanol from 1-Pentanol

| Compounds | Relative Volatility |
|---|---|
| None | 1.14 |
| Acetal | 1.45 |
| Dioxolane | 1.43 |
| Methyl acetate | 1.47 |
| Ethyl acetate | 1.46 |
| Isopropyl acetate | 1.43 |
| Propyl acetate | 1.4 |
| Butyl formate | 1.4 |
| Ethyl formate | 1.5 |
| Di-tert. butyl carbonate | 1.5 |
| Acetone | 1.55 |
| 2-Butanone | 1.43 |
| 2-Pentanone | 1.4 |
| 4-Methyl-2-pentanone | 1.4 |
| 3-Methyl-2-butanone | 1.48 |
| t-Butyl methyl ether | 1.55 |
| Ethyl ether | 1.45 |
| Isopropyl ether | 1.5 |
| Dimethoxymethane | 1.48 |
| Acetol | 1.43 |
| 1-Methoxy-2-propanol | 1.4 |
| 1,4 Dioxane | 1.42 |
| Butyraldehyde | 1.43 |
| Triethyl amine | 1.43 |
| Acetonitrile | 1.45 |
| Nitromethane | 1.43 |
| 2-Nitropropane | 1.43 |
| Nitroethane | 1.43 |
| Tetrahydrofuran | 1.5 |
| 2-Methoxyethanol | 1.4 |
| Salicylaldehyde | 1.4 |
| Benzene | 1.5 |
| Toluene | 1.42 |
| Cyclopentane | 1.6 |
| Hexane | 1.45 |
| Cyclohexane | 1.45 |
| Cyclohexene | 1.45 |

TABLE 3-continued

Effective Azeotropic Distillation Agents For Separating
2-Methyl-1-butanol & 3-Methyl-1-butanol from 1-Pentanol

| Compounds | Relative Volatility |
| --- | --- |
| p-Xylene | 1.43 |
| o-Xylene | 1.5 |
| Methyl cyclohexane | 1.48 |
| Heptane | 1.45 |
| 2,2,4-Trimethylpentane | 1.45 |
| Diethyl amine | 1.45 |

DETAILED DESCRIPTION OF THE INVENTION

I have discovered that certain organic compounds will effectively increase the relative volatility between 2-methyl-1-butanol & 3-methyl-1-butanol from 1-pentanol during rectification when employed as the agent in azeotropic distillation. They are acetal, dioxolane, methyl acetate, ethyl acetate, isopropyl acetate, propyl acetate, butyl formate, ethyl formate, di-tert. butyl carbonate, acetone, 2-butanone, 2-pentanone, 4-methyl-2-pentanone, 3-methyl-2-butanone, t-butyl methyl ether, ethyl ether, isopropyl ether, dimethoxymethane, acetol, 1-methoxy-2-propanol, 1,4-dioxane, butyraldehyde, triethyl amine, acetonitrile, nitromethane, 2-nitrpropane, nitroethane, tetrahydrofuran, 2-methoxyethanol, salicylaldehyde, benzene, toluene, cyclopentane, hexane, cyclohexane, cyclohexene, p-xylene, o-xylene, methyl cyclohexane, heptane, 2,2,4-trimethylpentane and diethyl amine.

THE USEFULNESS OF THE INVENTION

The usefulness or utility of this invention can be demonstrated by referring to the data presented in Tables 1, 2 and 3. All of the successful agents show that 2-methyl-1-butanol and 3-methyl-1-butanol can be separated from 1-pentanol by means of azetropic distillation and that the ease of separation is considerable.

WORKING EXAMPLE

Example 1

Fifty grams of a 2-methyl-1-butanol, 3-methyl-1-butanol and 1-pentanol mixture and fifty grams of toluene as the azeotrope forming agent were charged to a vapor-liquid equilibrium still and refluxed for two hours. The vapor composition was 72.5% 2-methyl-1-butanol - 3-methyl-1-butanol, 27.5% 1-pentanol; the liquid composition was 63.3% 2-methyl-1-butanol-3-methyl-1-butanol, 36.7% 1-pentanol.

This is a relative volatility of 1.5.

I claim:

1. A method for recovering 2-methyl-1-butanol and 3-methyl-1-butanol from a mixture of 2-methyl-1-butanol, 3-methyl-1-butanol and 1-pentanol which consists essentially of distilling a mixture consisting of 2-methyl-1-butanol, 3-methyl-1-butanol and 1-pentanol in the presence of an azeotrope forming agent, recovering the 2-methyl-1-butanol, 3-methyl-1-butanol and the azeotrope forming agent as overhead product and obtaining the 1-pentanol as bottoms product, wherein said azeotrope forming agent consists of one material selected from the group consisting of acetal, dioxolane, methyl acetate, isopropyl acetate, propyl acetate, butyl formate, ethyl formate, di-tert. butyl carbonate, acetone, 2-butanone, 2-pentanone, 4-methyl-2pentanone, 3-methyl-2-butanone, isopropyl ether, acetol, 1-methoxy-2-propanol, butytaldehyde, triethyl amine, acetonitrile, nitromethane, 2-nitropropane, nitroethane, tetrahydrofuran, 2-methoxyethanol, salicylaldehyde, benzene, toluene, cyclopentane, hexane, cyclohexane, cyclohexene, p-xylene, o-xylene, methyl cyclohexane, heptane, 2,2,4-trimethylpentane and diethyl amine.

* * * * *